United States Patent [19]

Kuboyama et al.

[11] Patent Number: 4,591,571

[45] Date of Patent: May 27, 1986

[54] FINE CARRIER PARTICLES SENSITIZED WITH ACYLATED ANTIBODY FOR ANTIGEN DETECTION

[75] Inventors: Morio Kuboyama, Tokyo; Yoshitsugu Harada, Yokohama; Akio Kawashiri, Fujimi; Eiji Takahashi, Funabashi, all of Japan

[73] Assignee: Morinaga Milk Industry Co., Ltd., Tokyo, Japan

[21] Appl. No.: 601,522

[22] Filed: Apr. 18, 1984

[30] Foreign Application Priority Data

Apr. 28, 1983 [JP] Japan .................................. 58-74123

[51] Int. Cl.[4] ........................................... G01N 33/546
[52] U.S. Cl. .................................... 436/533; 436/534; 436/547; 436/825; 530/387
[58] Field of Search ................ 436/533, 534, 547, 825

[56] References Cited

U.S. PATENT DOCUMENTS 4,418,152 11/1983 Hosaka ............................ 436/534 X
4,444,880 4/1984 Tom ..................................... 436/825
4,478,934 10/1984 Sato ................................. 436/547 X

OTHER PUBLICATIONS

"Enzyme-Immunoassay", E. T. Maggio, pp. 72–75, CRC Press, Boca Raton, 1980.
Chemical Abstracts, 87:182402j (1977).

Primary Examiner—Sidney Marantz
Attorney, Agent, or Firm—Jordan and Hamburg

[57] ABSTRACT

Reagents for detecting antigen contained in body fluid or urine according to the immunological agglutination or agglutination inhibition reaction and comprising an antibody adsorbed on fine carrier particle to be sensitized as an effective constituent, and is characterized by acylating said antibody.

Owing to such acylation, the reagent can correctly detect antigen without any influence of substance contained in sample which has inevitably caused nonspecific agglutination reaction according to the prior art.

6 Claims, No Drawings

FINE CARRIER PARTICLES SENSITIZED WITH ACYLATED ANTIBODY FOR ANTIGEN DETECTION

BACKGROUND OF THE INVENTION

Detection or concentration determination of various hormones, proteins, medicines and metabolites thereof involved in body fluids or excreted fluid has played an important role as clinical analysis in diagnosis of diseases, judgement of prognosis and decision of therapeutics. Such determination or quantitative analysis has been made physicochemically, biochemically or immunologically. Above all immunological methods such as radioimmunoassay (RIA), enzyme immunoassay (EIA) have widely been used in the clinical analysis since a very small ammount of substances contained in body fluids or urine may be determined specifically and in good reproducibility. Method for detection of a very small amount of substances in body fluids or urine according to immunological agglutination or agglutination inhibition reaction has also widely been used.

The method by virtue of agglutination or agglutination inhibition is carried out for instance by injecting an antigen into a mammal to produce the antibody specific thereto, applying the antigen and/or antibody to fine carrier particle such as red blood cells, latex polymer particles to be adsorbed, reacting with antigen or antibody, and macroscopically observing or instrumentally determining the state of agglutination or agglutination inhibition so as to recognize presence or absence of antigen or determine concentration thereof.

The so-called "nonspecific agglutination reaction", which means agglutinations other than agglutination specifically caused by immunological antigen-antibody reaction and which is caused by some substances existing in body fluids or urine, may considerably influence on the method of detection according to the agglutination or agglutination inhibition reaction using such carrier. This comes into question particularly in case of the method wherein antibody adsorbed by carrier is reacted with antigen in test sample so as to detect presence or absence of agglutination of the sensitized carrier or quantitatively analyze concentration of antigen. When such nonspecific agglutination occurs, there is a possibility that false judgement holding existence of the antigen in body fluid or urine despite of absence thereof or lower concentration thereof despite of higher concentration of antigen is given, which may considerably influence on the precision and the reliability of the method as to detect presence or absence of antigen, or determine concentration of antigen and consequently on diagnosis of diseases, judgement of prognosis or decision of therapeutics.

It is thus very important by the reasons referred to above to exclude the nonspecific agglutination reaction in the method for detecting antigen in body fluid or urine by means of immunological agglutination or agglutination inhibition reaction. Hithertofore various methods have been proposed for excluding such undesired reaction, among which are method specifying pH value and kinds of buffer solution for the reagent (Japanese Early Opened Patent Application Gazettes Nos. 35754/82 and 182168/82), method filtering to remove the substance causing such nonspecific agglutination reaction (Japanese Early Opened Patent Application Gazettes Nos. 31696/72, 146022/80, 182170/82; Japanese Patent Publication Gazettes Nos. 43038/77, 24509/82), method adding specific additive to the reagent to be used (Japanese Early Opened Patent Application Gazettes Nos. 82230/75, 12419/80, 1970/82, 9723/82, 59167/82; Japanese Patent Publication Gazettes Nos. 12741/68, 11407/74) and method decomposing antibody with using hydrolytic enzyme (Japanese Early Opened Patent Application Gazette No. 139595/79).

Although many proposals have been made for excluding undesired nonspecific agglutination which is very interested in the field of clinical analysis, any of said methods are not satisfactory in that it is difficult to completely and selectively exclude such undesired reactions, that specific agglutinative ability is lost even if the reaction can selectively be excluded that antibody structure which is recognized as a cause of nonspecific agglutination with substances such as rheumatoid factor and complement, or that very complicated preparation of the reagent is necessitated for attaining the purpose.

On the otherhand, chemical modification of protein with an acylating agent has widely been carried out for the purpose of study of structure or improvement of thermal stability of protein (Japanese Patent Publication Gazette No. 29039/82). As for the other methods for chemical modification of antibody, substitution with 2, 4-dinitrophenyl group (Japanese Early Opened Patent Application Gazette No. 139595/79) and succinylation ("Nature" Vol. 210, page 536, 1966) has been known. The former is aimed at strong adsorption of antibody to fine carrier particle and the latter relates to preparation of succinylated γ-globulin and fundamental study of nature thereof. At any rate it has never been known yet that acylated antibody is effective for excluding immunologically nonspecific agglutination or agglutination inhibition reaction.

The inventors have tried to develop a reagent for readily and quickly detecting antigen contained in body fluids or urine according to immunological agglutination reaction without causing undesired nonspecific agglutination to find out that it is possible to astonishingly completely exclude influence by substances in body fluids or urine to cause the nonspecific agglutination by using fine carrier particle sensitized with acylated antibody so as to make it possible to detect antigen in test sample in high precision, on which finding the present invention is based.

SUMMARY OF THE INVENTION

Thus an object of this invention is to provide a reagent for detecting antigen without influence of substances contained in a test sample to cause undesired nonspecific agglutination.

The other object is to provide such reagent for analyzing antigen in body fluids or urine readily, quickly and in good reproducibility.

The objects can be attained according to the invention by chemically modifying antibody with an acylating agent, which antibody is adsorbed on fine carrier particle to be used as effective constituent of the reagent for detecting antigen.

DETAILED DESCRIPTION OF THE INVENTION

Antibody to be used in the invention is prepared immunologically by applying the so-called high molecular weight antigens such as proteins, polypeptides, polysaccharides, lipids which form antigen-antibody reaction precipitate when reacted with antigen or the so-called low molecular weight antigens, haptens such as steroids, haptenes for medicines which do not form precipitate although antigen-antibody reaction occurs to a mammal such as guinea pig, rabbit, goat, sheep, and equine, among which rabbit, goat and sheep are more preferable according to the usual method. There is no particular limitation in the kind of antigen.

Antibody is obtained as antiserum containing antibody specific to respective antigen. Such antiserum may be used in the invention as it is. Since animal serum contains various substances having biological activity, immunoglobulin containing antibody may be separated according to the usual method from said antiserum or specific antibody itself may be obtained according to the usual purification method to be used for the invention. Various methods have been established for separation of immunoglobulin, among which method of ammonium sulfate precipitation, DEAE cellulose column chromatography and combination thereof are usual at the present. As for purification, affinity chromatography is usually used at the present and antibody purified thereby may be used in the invention.

According to the invention antibody obtained as in the above is chemically modified usually with use of an acylating agent. Antibody is dissolved in water or buffer solution with adjusting pH value in the range of 7–10, to which acylating agent of 0.2–200% and more preferably 0.5–100% by weight relative to antibody protein is gradually added with stirring, during which pH is kept at 6–10 and more preferably 7–9 by adding an alkaline solution. After completion of acylating agent addition, the solution is dialyzed against water, salt solution or buffer solution to remove unnecessary acylating agent and obtain acylated antibody.

Whatever acylating agent may be used, but it is necessary or preferable therefor that specific activity of antibody is not lost due to the chemical modification, that nonspecific agglutination reaction can be excluded in the immunological reaction, that chemical modification may quantitatively proceed, that acylating agent may be readily removed after the chemical modification, and that treatment of acylating agent is easy and cost is low.

Among the acylating agents are monocarboxylic anhydrides such as acetic anhydride, ethoxyformic anhydride; dicarboxylic anhydrides such as succinic anhydride, maleic anhydride, citraconic anhydride, tetrafluorosuccinic anhydride, 3,3-tetramethyleneglutaric anhydride; polycarboxylic anhydrides; and halides as well as esters thereof, among which anhydrides of succinic, maleic and acetic acids are particularly preferable.

When antibody is treated with the acylating agent, electric charge of antibody as protein is changed. For instance when acylating antibody with acetic anhydride, $\epsilon$-amino group of lysine in antibody protein molecule is succinylated so as to substitute positive charge of one $\epsilon$-amino group for negative charge of one carboxyl group of succinic acid, as a result of which electric charge of whole antibody protein molecule is considerably shifted to the negative side in comparison with that of untreated antibody. Such electric charge shift of acylated antibody is varied depending on the kind of the acylating agent, concentration thereof, conditions of treatment and the like. Optimal conditions under which acylated antibody does not cause nonspecific agglutination may readily be selected depending on the kind of the acylating agent to be used.

Fine carrier particle used in the invention may be any of latex polymer particles, red blood cells, some inorganic compound particles and the like, among which latex polymer particles are particularly preferable. There are various latex polymer particles, but fine particles of polystyrene, polybutadiene, styrene-butadiene copolymer which have no active group and are chemically and serologically innert, are preferable, among which polystyrene latex particles are particularly preferable. Particle diameter of latex polymer particle used is preferably in the range of $0.05-5\mu$ and more preferably of $0.1-2\mu$.

Acylated antibody is adsorbed on such fine carrier particle according to the usual method. Carrier particles are suspended in buffer solution of pH value. The suspension is added with agitation to buffer solution to which acylated antibody is dissolved so that the carrier is sensitized with antibody. The amount of acylated antibody to be used therefor is suitably selected depending on various conditions such as its kind and its sensitivity.

Temperature of sensitization is in the range of 4°–70° C. and more preferably of 25°–56° C., while time of sensitization is in the range between a few minutes and a few hours, and more preferably of 0.5–3 hours. Fine carrier particle sensitized with acylated antibody is subjected to centrifugal separation to obtain precipitate. The precipitate itself or product obtained by resuspending the precipitate in buffer solution of pH 6–10 and drying may be used as the reagent. It is possible to detect antigen by applying test sample directly to the dried reagent or to which the reagent is suspended in buffer solution before use.

The precipitate obtained by said centrifugal separation may be redispersed in buffer solution of pH 6–10 to prepare the reagent in liquid. In order to improve storage and keep stability for the reaction some stabilizer may be added to such liquid reagent. As for the stabilizer, some proteins which do not relate to immunological reaction saccharides, and more preferably serum albumin is used. Concentration of carrier particle sensitized with acylated antibody in the buffer solution is in the range of 0.01–3.0%, and more preferably 0.05–1.5% by weight.

The liquid reagent prepared as in the above is used as in the following explanation. A fixed amount of a test sample of body fluids or urine which may be subjected to prior treatment such as dilution is taken on a slide or in a tube to which a fixed amount of the reagent of the invention is added to be mixed homogeneously. Agglutination occurred is observed macroscopically or determined optically. In the case of macroscopical methods, the reagent of the invention is mixed with test sample of body fluids or urine containing antigen on a slide or in a tube and then presence or absence of agglutination is observed. On the other hand, in the case of optical methods the above mixture in a tube is determined with the change of transmittance, light scattering or turbidity in a optical cell. By means of suspending of the dried reagent of the invention in buffer solution just before use, it is used as same as liquid reagent in the above. When appling test sample directly to the dried reagent of the invention, a fixed amount of body fluids or urine is added to dried reagent, mixed and resuspended homogeneously, and determined presence or absence of agglutination macroscopically or optically as same as the liquid reagent of the invention. When the reagent is in the state of solid, it may be dispersed in buffer solution in advance as refered to above. Then it is observed macroscopically or by means of optical instrument whether agglutination is caused or not.

The invention will be explained further in detail based on some exemplifying tests.

TEST 1

(1-1) Preparation of Antibody (Anti-HCG Immunoglobulin)

Highly purified human chorionic gonadotropin which is to be obbreviated as HCG hereinafter was applied to goat to obtain anti-HCG serum. Saturated solution of ammonium sulfate in the amount of 25 ml was added to 50 ml of said serum. After agitation for 20 min. in a ice bath, centrifugation under refrigeration by 10,000 r.p.m. was carried out for 20 min. to recover resulting precipitate, which was dissolved in 30 ml of water and added with 15 ml saturated solution of ammonium sulfate. Centrifugation was carried out under refrigeration for 20 min. to obtain resulting precipitate. The same treatement was repeated further two times. Finally obtained precipitate was dissolved in 0.01M phosphate buffer solution (pH 8.0), from which immunoglobulin was separated according to gel-filtration with use of Sephadex G-25 column equilibrated in advance with the same buffer solution. Obtained immunoglobulin fraction was subjected to freeze-drying to obtain about 500 mg anti-HCG immunoglobulin.

(1-2) Acylation of Antibody (Anti-HCG Immunoglobulin)

Anti-HCG immunoglobulin obtained in (1-1) in the amount of 200 mg was dissolved in 0.1M NaCl solution added with NaOH (pH 8) to be of 1% concentration and cooled in ice water bath. To said solution was gradually added 40 mg of solid succinic anhydride with stirring. In order to avoid lowering of pH of the solution, 1N NaOH was added to keep the value higher than 7. After succinic anhyide dissolution, agitation was continued for further 1 hour. After completion of the reaction, the solution was subjected to dialysis against 0.1M NaCl solution adding NaOH (pH 8.5) overnight to remove unreacted succinic acid, whereby about 202 mg of succinylated anti-HCG immunoglobulin was obtained.

(1-3) Preparation of Fine Carrier Particle Sensitized with Acylated Antibody (Succinylated Anti-HCG Immunoglobulin)

Succinylated anti-HCG immunoglobulin obtained in (1-2) was dissolved in glycine buffer solution (pH 8.2) to be of concentration of 1 mg/ml. Said solution of 1 part by volume was mixed with 1 part by volume of suspension which was prepared by dispersing polystyrene latex particles of $0.220\mu$ size (Dow Chemical) in glycine buffer solution (pH 8.2) in the concentration of 2% to be held at 37° C. for 1 hour so that succinylated anti-HCG immunoglobulin is adsorbed on polystyrene latex particle. Then centrifugation was carried out by 10,000 r.p.m. for 20 min. to remove anti-HCG immunoglobulin unadsorbed and collect sensitized latex particles precipitated whereby about 2.5 g of carrier particle sensitized with succinylated anti-HCG immunoglobulin was obtained.

(1-4) Preparation of Reagent for Antigen Detection

Said latex carrier particles sensitized with succinylated anti-HCG immunoglobulin in the amount of 1 g was suspended again in 100 ml of glycine buffer solution (pH 8.2) containing 0.1% of rabbit serum albumin to be abbreviated RSA hereinafter as a stabilizer to prepare the reagent solution.

(1-5) Sensitivity by Means of Standard HCG Solution

Sensitivity of the reagent according to the invention was determined as follows. 50 $\mu$l solution of standard HCG dissolved in 0.1% RSA containing glycine buffer solution (pH 8.2) by the concentration shown in Table 1, 25 $\mu$l of said buffer solution and 25 $\mu$l of the reagent solution were respectively dropped on the slide glass to be mixed together. Then the slide was slowly rotated about 3 min. to macroscopically observe exsistence or nonexsistence of agglutination.

As control, the latex polymer reagent sensitized with anti-HCG immunoglobulin prepared by using anti-HCG immunoglobulin manufactured as in (1-1) similarly but instead of succinylated anti-HCG immunoglobulin of the invention. The test results were as shown in Table 1.

TABLE 1

| Standard HCG Solution (IU/ml) | Macroscopic Observation | |
|---|---|---|
| | Reagent of Invention | Reagent of Prior Art |
| 0.1 | − | − |
| 0.25 | − | − |
| 0.5 | − | − |
| 1.0 | + | + |
| 2.5 | + | + |
| 5.0 | + | + |

+ means positive agglutination and
− means negative agglutination

As seen from Table 1, the reagent according to the invention has the same sensitivity (1 IU/ml) with that of the reagent prepared by the prior art and there was observed no influence of succinylation on the sensitivity.

(1-6) Test for Nonspecific Agglutination Reaction Caused by Nonpregnant Woman Urine On the slide glass respective 50 $\mu$l of urine was dropped which was obtained by centrifugation to remove precipitate in respect of 20 nonpregnant women urine samples. Existence of agglutination was macroscopically observed similarly as in (1-5). As control the same reagent as in (1-5) was used. The results are shown in Table 2.

TABLE 2

| Sample | Reagent of Invention | Reagent of Prior Art | Sample | Reagent of Invention | Reagent of Prior Art |
|---|---|---|---|---|---|
| 1 | − | + | 11 | − | + |
| 2 | − | + | 12 | − | + |
| 3 | − | + | 13 | − | + |
| 4 | − | + | 14 | − | + |
| 5 | − | ± | 15 | − | + |
| 6 | − | + | 16 | − | + |
| 7 | − | + | 17 | − | ± |
| 8 | − | + | 18 | − | + |
| 9 | − | + | 19 | − | + |
| 10 | − | + | 20 | − | + |

+ means positive agglutination,
± means weak positive agglutination and
− means agglutination As seen from Table 2, the reagent according to the invention did not cause any nonspecific agglutination, while the reagent prepared by the prior art caused agglutination or weak agglutination on the all test samples of nonpregnant women urines. This means the reagent according to the prior art may occur nonspecific agglutination and can not correctly detect HCG regarding to all test samples, while this invention has astonishingly succeeded to overcome the disadvantage of the prior art.

(1-7) Detection for HCG in Pregnant Woman Urine

The same observation was made as in (1-6) in respect of 20 samples of urines of early stage pregnant women. For reference, concentration of HCG respective urine sample was determined according to RIA by Ratky et al (British Journal of Haematology, Vol. 30, page 145, 1975). The results are shown in Table 3.

TABLE 3

| Sample | Reagent of Invention | Reagent of Prior Art | RIA (IU/ml) |
|---|---|---|---|
| 1 | + | + | 8.4 |
| 2 | + | + | 2.1 |
| 3 | + | + | 3.5 |
| 4 | − | + | 0.7 |
| 5 | + | + | 5.2 |
| 6 | − | + | 0.5 |
| 7 | + | + | 1.6 |
| 8 | + | + | 2.2 |
| 9 | + | + | 6.6 |
| 10 | + | + | 2.0 |
| 11 | + | + | 4.6 |
| 12 | + | + | 3.1 |
| 13 | − | + | 0.4 |
| 14 | ± | + | 1.1 |
| 15 | + | + | 3.5 |
| 16 | + | + | 8.7 |
| 17 | − | + | 0.5 |
| 18 | − | + | 0.7 |
| 19 | + | + | 2.1 |
| 20 | + | + | 4.3 |

+ means positive agglutination,
± means weak positive agglutination and
− means negative agglutination Since the detection limit of the reagent of the invention was set as 1 IU/ml as to HCG, there was observed no agglutination in respect of five samples (Nos. 4, 6, 13, 17 and 18) where HCG concentration respectively under the limit of said detection sensitivity, which corresponds to test results according to RIA. The reagent prepared by the prior art, however, caused agglutination also on the samples in which HCG concentration was below the limit of detection sensitivity.

TEST 2

(2-1) Preparation of Antibody
(Anti-Estriol-16α-glucuronide Immunoglobulin)

Estriol-16α-glucuronide to be abbriviated as E3-16αG hereinafter and bovine serum albumin to be abbriviated as BSA hereinafter were chemically bound according to the usual method to obtain E3-16αG-BSA conjugate which was applied to rabbit. Obtained anti-E3-16αG-BSA serum in the amount of 50 ml was subjected to dialysis against 0.01M phosphoric acid buffer solution (pH 8.0) in the amount of 10 l overnight so that E3-16αG-BSA anti-body was adsorbed by BSA, which was subjected to chromatography with using DEAE cellulose in advance equilibrated with said buffer solution. From recovered immunoglobulin fraction, about 250 mg anti-E3-16αG immunoglobulin was obtained.

(2-2) Acylation of Antibody 100 mg Anti-E3-16αG immunoglobulin obtained as in (2-1) was dissolved in 0.1M NaCl (pH 9) to be of 1% concentration and cooled in ice water bath. 5 mg of solid maleic anhydride was added with agitation to said solution, during which 0.5N NaOH was added in order to keep pH value above 7. Agitation was continued for further 1 hour after dissolution of maleic anhydride. Aftger completion of the reaction, the solution was subjected to dialysis against distilled water of which pH was adjusted at 8.5 to remove unreacted maleic acid and subjected to freeze-drying, whereby about 98 mg maleylated anti-E3-16αG immunoglobulin was obtained.

(2-3) Preparation of Latex Particles Sensitized with Maleylated Anti-E3-16αG Immunoglobulin Maleylated anti-E3-16αG immunoglobulin obtained in (2-2) was dissolved in barbital buffer solution (pH 7.8) to be of concentration of 1 mg/ml. Said solution of 1 part by volume was mixed with 1 part by volume of suspension which was prepared by dispersing polystyrene latex particles of 0.198μ size (Dow Chemical) in barbital buffer solution (pH 7.8) in the concentration of 2% to be held at 45° C. for 1 hour so that maleylated anti-E3-16αG immunoglobulin is adsorbed by polystyrene latex particle. Then centrifugation was carried out by 10,000 r.p.m. for 20 min. to remove maleylated anti-E3-16αG immunoglobulin unadsorbed and obtained about 1.5 g of precipitated latex particles sensitized with maleylated anti-E3-16αG immunoglobulin.

(2-4) Preparation of Reagent for Antigen Detection

Said latex carrier particle sensitized with maleylated anti-E3-16αG immunoglobulin in the amount of 0.5 g was again suspended in 100 ml of barbital buffer solution (pH 7.8) containing 0.1% of RSA as a stabilizer to prepare the reagent solution.

(2-5) Preparation of Latex Particles Reagent Sensitized with E3-16αG-RSA

According to the process described in Example 1 of Japanese Early Opened Patent Application Gazette 8715/79, E3-16αG-RSA was prepared in which E3-16αG is bound two molecules per one molecule of RSA. The reagent sensitized with said E3-16αG-RSA was obtained according to the method described as in (2-4). Detection sensitivity of E3-16αG in the obtained reagent was adjusted at 0.2 μg/ml.

(2-6) Determination of Sensitivity by Means of Standard E3-16αG Solution

Sensitivity for agglutination inhibition according to the two sorts of reagents obtained as in (2-4) and (2-5) was determined as follows.

As shown in Table 4, 50 μl of solution of standard E3-16αG in barbital buffer solution (pH 7.8) and 20 μl of sensitized reagent obtained as in (2-5) were respectively dropped on the slide glass to be mixed together, in which 20 μl of the reagent obtained as was dropped so as to macroscopically observe presence of agglutination after slowly rotating of the slide for three min.

As control, the latex particle reagent sensitized with anti-E3-16αG immunoglobulin was prepared according to the methods described in (2-3) and (2-4) with using anti-E3-16αG immunoglobulin obtained as in (2-1) instead of maleylated anti-E3-16αG immunoglobulin. The same operation as in the above was repeated so as to macroscopically observe the presence or absence of agglutination.

The test results were as shown in Table 4.

TABLE 4

| Standard E3-16αG Solution (μg/ml) | Reagent of Invention | Reagent of Prior Art |
|---|---|---|
| 0.05 | + | + |
| 0.1 | + | + |
| 0.2 | − | − |
| 0.5 | − | − |
| 1.0 | − | − |

+ means positive agglutination and
− means negative agglutination

As seen from said Table, the reagent according to the invention shows the same detection sensitivity (0.2 μg/ml) with that of the reagent prepared by the prior art and there was found no influence of maleylation of anti-E3-16αG immunoglubulin on the detection sensitivity.

(2-7) Detection for E3-16αG in Urine

The same observation was made as in (2-6) in respect of 10 samples of urines of early stage pregnant women. For reference, concentration of E3-16αG in the respective urine sample was determined according to RIA by Stanczk et al (Journal of Steroid Biochemistry, Vol. 10, page 443, 1979). The results are shown in Table 5.

TABLE 5

| Sample | Reagent of Invention | Reagent of Prior Art | RIA (μg/ml) |
|---|---|---|---|
| 1 | + | + | 0.02 |
| 2 | − | + | 0.60 |
| 3 | − | + | 0.34 |
| 4 | − | + | 1.10 |
| 5 | + | + | 0.08 |
| 6 | − | + | 0.24 |
| 7 | + | + | 0.02 |
| 8 | − | + | 0.27 |
| 9 | − | + | 0.61 |
| 10 | + | + | 0.14 |

+ means positive agglutination and
− means negative agglutination

Since the detection limit of the reagent of the invention was set as 0.2 μg/ml as to E3-16αG there was observed agglutination in respect of four samples (Nos. 1, 5, 7 and 10) where E3-16αG concentration respectively was below said limit of the detection sensitivity, which correspond to the test results according to RIA. The reagent prepared by the prior art, however, caused agglutination also on the samples in which E3-16αG concentration was above limit of detection sensitivity and determined to be below concentration of limit of detrection sensitivity.

TEST 3

(3-1) Preparation of Antibody (Anti-Human Fibrinogen Immunoglobulin)

Highly purified human fibrinogen to be abbreviated as Fg hereinafter was applied to rabbit to obtain anti-Fg serum, which was applied in the amount of 10 ml to the column filled with Fg-Sepharose 4B prepared by usual method. Then 0.01M phosphate buffer solution (pH 8.0) was applied to the column to be washed and remove all unnecessary substances other than anti-Fg immunoglobulin. With using 0.2M glycine-hydrochloric acid buffer solution (pH 2.3) there was eluted anti-Fg immunoglobulin of which pH value was kept at 7-8. After adjustment of pH of the eluate at 7.5, it was subjected to freeze-drying. This operation was repeated to obtain about 50 mg of anti-Fg immunoglobulin.

(3-2) Acylation of Antibody 50 mg Anti-Fg immunoglobulin obtained as in (3-1) was dissolved in water to be of 0.5% concentration and cooled in ice water bath. 6 g of solid sodium acetate was added so as to be completely dissolved in said solution, to which 25 μl acetic anhydride was gradually added with keeping agitation and cooling. After completion of the addition, the reaction was continued for further 1 hour. After completion of the reaction, said solution was subjected to dialysis against 0.1M NaCl containing glycine buffer solution (pH 8.2) overnight so as to remove acetic acid and obtain about 45 mg acetylated anti-Fg immunoglobulin.

(3-3) Preparation of Latex Particles Sensitized with Acetylated Anti-Fg Immunoglobulin Acetylated anti-Fg immunoglobulin obtained as in (3-2) was dissolved in glycine buffer solution (pH 8.6) to be of concentration of 0.3 mg/ml. Said solution of 1 part by volume was mixed with 1 part by volume of suspension which was prepared by dispersing polystyrene latex particles of 0.721μ size (Dow Chemical) in glycine buffer solution (pH 8.6) in the concentration of 2% which was followed by the same operation as described in Test 1 to obtain about 80 ml reagent of the invention containing 1.2% latex particles sensitized with acetylated anti-Fg immunoglobulin.

(3-4) Measurement of Sensitivity by Means of Standard Fg Solution

Sensitivity of the reagent according to the invention obtained as in (3-3) was determined as follows.

Twenty five microliter of the reagent of the invention and 75 μl of the solution dissolved standard Fg in 0.2% RSA containing glycine buffer solution (pH 8.6) by the concentration shown in Table 6 was respectively dropped on the slide glass so as to macroscopically observe the presence of agglutination according to the same operation as in Test 1 (1-5).

As control, the reagent prepared by the prior art was prepared by sensitizing latex particle with anti-Fg immunoglobulin which was obtained as in (3-1) instead of acetylated anti-Fg immunoglobulin so as to similarly observe the presence of agglutination.

The results are shown in Table 6.

TABLE 6

| Standard Fg Solution (μg/ml) | Reagent of Invention | Reagent of Prior Art |
|---|---|---|
| 0.1 | − | − |
| 0.25 | − | − |
| 0.5 | + | + |
| 1 | + | + |
| 2 | + | + |
| 5 | + | + |
| 10 | + | + |

+ means positive agglutination and
− means negative agglutination

As seen from said Table, the reagent of the invention has the same detection sensitivity (0.5 μg/ml) as that of said usual reagent. There was recognized no influence of acetylation of anti-Fg immunoglobulin on the sensitivity of detection.

(3-5) Detection of Nonspecific Agglutination by Means of Healthy Man Urine

In respect of 10 healthy men urines, the tests were made. Each raw urine of 75 μl was dropped on the slide glass, on which 25 μl of the reagent of the invention obtained as in (3-3) was dropped so as to macroscopically observe the presence of agglutination with slowly rotating the slide for 3 min. As control the same reagent as shown in (3-4) was used to similarly observe agglutination.

The results are shown in Table 7.

TABLE 7

| Sample | Reagent of Invention | Reagent of Prior Art | Sample | Reagent of Invention | Reagent of Prior Art |
|---|---|---|---|---|---|
| 1 | − | + | 6 | − | + |
| 2 | − | + | 7 | − | + |
| 3 | − | + | 8 | − | + |
| 4 | − | + | 9 | − | + |
| 5 | − | + | 10 | − | + |

+ means positive agglutination and
− means negative agglutination

There was not found any nonspecific agglutination according to the invention, while nonspecific agglutination was observed in respect of all test samples according to the reagent prepared by the prior art.

(3-6) Detection of Urine Fibrin or Fibrin Degradation Product

With using urines as test samples taken from 10 persons suspected to be of intravascular coagulation, detection of fibrin or fibrin decomposition product to be abbreviated as FDP hereinafter in urine was carried out according to the same operation as in (3-5). For reference, FDP concentration in urine was determined according to RIA by Ratky et al as referred to above. The results are shown in Table 8.

TABLE 8

| Sample | Reagent of Invention | Reagent of Prior Art | RIA (μg/ml) |
|---|---|---|---|
| 1 | + | + | 2.1 |
| 2 | + | + | 0.33 |
| 3 | + | + | 0.63 |
| 4 | − | + | 0.21 |
| 5 | − | + | 0.13 |
| 6 | + | + | 1.60 |
| 7 | − | + | 0.15 |
| 8 | + | + | 8.3 |
| 9 | − | + | 0.10 |
| 10 | − | + | 0.17 |

+ means positive agglutination and
− means negative agglutination

According to the reagent of the invention there was observed no agglutination regarding five samples (Nos. 4, 5, 7, 9 and 10) in which FDP concentration in the respective sample was below the limit of detection sensitivity the reagent which corresponds respectively to the results of the determination according to RIA, while the usual reagent caused agglutination also on the samples in which FDP concentration was below the limit of detection sensitivity which did not accord with the RIA results.

From the experimental results referred to above, followings can be concluded;

(1) The invention makes it possible to detect antigen in the test sample without any influence of substances contained in the sample to cause nonspecific agglutination.

(2) Reproducibility of detection of antigen in the test sample is quite excellent.

(3) Detection of antigen in the test sample is possible without necessity of any previous treatment as to the fresh sample just after taking out.

(4) Preparation of the reagent is very simple.

What is claimed is:

1. In a reagent comprising antibody-sensitized fine carrier particles for detecting antigen in body fluids by agglutination or agglutination inhibition, the improvement comprising:
   antibody-sensitized fine carrier particles wherein the antibody has been chemically modified with an acylating agent.

2. The reagent according to claim 1, wherein the acylating agent is selected from the group consisting of monocarboxylic anhydrides, dicarboxylic anhydrides, polycarboxylic anhydrides, halides thereof and esters thereof.

3. The reagent according to claim 2, wherein the acylating agent is selected from the group consisting of anhydrides of succinic, maleic and acetic acids.

4. The reagent according to claim 1, wherein the antibody-sensitized fine carrier particles are suspended in a buffer solution of a concentration range of 0.01–3.0% by weight.

5. The reagent according to claim 4, wherein the pH of the buffer solution is 6–10.

6. The reagent according to claim 1 further comprising an immunologically inert protein and/or saccharide as a stabilizer.

* * * * *